United States Patent
Liao et al.

(10) Patent No.: US 11,766,416 B2
(45) Date of Patent: Sep. 26, 2023

(54) COMPOSITIONS OF β-AMINOISOBUTYRIC ACID AND METHODS FOR USE THEREOF

(71) Applicant: Nanjing Nutrabuilding Bio-tech Co., Ltd., Nanjing (CN)

(72) Inventors: Qilin Liao, Lewisville, TX (US); Shawn Wells, Lewisville, TX (US)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 112 days.

(21) Appl. No.: 17/382,476

(22) Filed: Jul. 22, 2021

(65) Prior Publication Data

US 2022/0054441 A1   Feb. 24, 2022

Related U.S. Application Data

(60) Provisional application No. 63/055,071, filed on Jul. 22, 2020.

(51) Int. Cl.
| | |
|---|---|
| *A61P 3/00* | (2006.01) |
| *A61P 3/02* | (2006.01) |
| *A61P 3/04* | (2006.01) |
| *A61P 3/06* | (2006.01) |
| *A61P 3/10* | (2006.01) |
| *A61K 31/197* | (2006.01) |

(52) U.S. Cl.
CPC .............. *A61K 31/197* (2013.01); *A61P 3/04* (2018.01); *A61P 3/10* (2018.01)

(58) Field of Classification Search
CPC ...... A61P 3/00; A61P 3/02; A61P 3/04; A61P 3/06; A61P 3/10; A61K 31/197
See application file for complete search history.

(56) References Cited

PUBLICATIONS

Barbera' et al. "Peroxisome Proliferator-activated Receptor a Activates Transcription of the Brown Fat Uncoupling Protein-1 Gene," The Journal of Biological Chemistry, Jan. 2001, vol. 276, No. 2, pp. 1486-1493.
Begriche et al. "β-aminoisobutyric acid prevents diet-induced obesity in mice with partial leptin deficiency," Obesity, Sep. 2008, vol. 16, No. 9, pp. 2053-2067.
Jung et al. "BAIBA attenuates insulin resistance and inflammation induced by palmitate or a high fat diet via an AMPK-PPARδ-dependent pathway in mice," Diabetologia, Sep. 2015, vol. 58, No. 9, pp. 2096-2105.
Kitase et al. "β-aminoisobutyric Acid, L-BAIBA, Is a Muscle-Derived Osteocyte Survival Factor," Cell Reports, Feb. 2018, vol. 22, pp. 1531-1544.
Liang et al. "PGC-1α: a key regulator of energy metabolism," Advances in Physiology Education, Dec. 2006, vol. 30, pp. 145-151.
Lira et al. "PGC-1α regulation by exercise training and its influences on muscle function and insulin sensitivity," American Journal of Phyiology-Endocrinology and Metabolism, Aug. 2010, vol. 299, pp. E145-161.
Maisonneuve et al. "Effects of zidovudine, stavudine and β-aminoisobutyric acid on lipid homeostasis in mice: possible role in human fat wasting," Antiviral Therapy, Oct. 2004, vol. 9, No. 5, pp. 801-810.
Note et al. "Mitochondrial and Metabolic Effects of Nucleoside Reverse Transcriptase Inhibitors (NRTIs) in Mice Receiving One of Five Single- and Three Dual-NRTI Treatments," Antimicrobial Agents and Chemotherapy, Nov. 2003, vol. 47, No. 11, pp. 3384-3392.
Roberts et al. "β-aminoisobutyric acid induces browning of white fat and hepatic β-oxidation and is inversely correlated with cardiometabolic risk factors," Cell Metabolism, Jan. 2014, vol. 19, No. 1, pp. 96-108.
Ruth "New Developments in Obesity," Year Book of Endocrinology, 2012, 1st Ed., Chapter 3—Obesity, pp. 114-116.
Shi et al. "β-aminoisobutyric acid attenuates hepatic endoplasmic reticulum stress and glucose/lipid metabolic disturbance in mice with type 2 diabetes," Scientific Reports, Feb. 2016, vol. 6, article 21924, 12 pages.
Smith et al. "The determination of β-amino-isobutyric acid in urine," Clinica Chimica Acta, Jul. 1963, vol. 8, No. 4, pp. 614-620.
Solem et al. "The absolute configuration of β-aminoisobutyric acid in human serum and urine," Clinica Chimica Acta, Feb. 1974, vol. 50, No. 3, pp. 393-403.
Tanianskii et al. "Beta-aminoisobutyric acid as a novel regulator of carbohydrate and lipid metabolism," Nutrients, Feb. 2019, vol. 11, No. 3, Article 524, 15 pages.
Vemula et al. "Gaussian and linear deconvolution of LC-MS/MS chromatograms of the eight aminobutyric acid isomers," Analytical Biochemistry, Jan. 2017, vol. 516, pp. 75-85.

*Primary Examiner* — Bruck Kifle
(74) *Attorney, Agent, or Firm* — ANOVA LAW GROUP PLLC

(57) ABSTRACT

Compositions of β-aminoisobutyric acid (BAIBA), and methods of using the same to achieve a physiological objective, are provided. Compositions of BAIBA having enantiomeric purity, in which a selected proportion of the BAIBA is L-β-aminoisobutyric acid (L-BAIBA) and/or a selected proportion of the BAIBA is D-β-aminoisobutyric acid (D-BAIBA), are also provided.

15 Claims, 7 Drawing Sheets

COMPOSITIONS OF β-AMINOISOBUTYRIC ACID AND METHODS FOR USE THEREOF

CROSS-REFERENCE TO RELATED APPLICATION

This application claims the benefit of priority under 35 U.S.C. § 119(e) to U.S. Provisional Patent Application 63/055,071, filed 22 Jul. 2020, the entirety of which is incorporated herein by this reference.

FIELD

The present disclosure relates generally to β-aminoisobutyric acid (BAIBA), and particularly to BAIBA compositions in which the BAIBA includes L-β-aminoisobutyric acid (L-BAIBA) and methods of use thereof to improve the effectiveness of exercise in a subject.

BACKGROUND

Obesity is a chronic disease that afflicts an increasing proportion of the world population, particularly in the developed world and is associated with decreased life span and numerous medical problems. In particular, obesity may eventually lead to, and/or increases the risk of contracting, such diseases and conditions as cholelithiasis, coronary heart disease, hepatic steatosis, hyperlipidemia, hypertension, insulin resistance, type 2 diabetes, and other cardiovascular diseases. Considering these effects of obesity and its increasing prevalence, a significant amount of research effort has been directed toward the development of therapeutic drugs and other treatments that may be useful in reducing body weight and/or body fat in humans.

Recently, β-aminoisobutyric acid (BAIBA) has generated interest in the scientific literature as a potential treatment for obesity and related conditions, such as pre-obesity and hyperglycemia. This interest is due to BAIBA's observed effect of reducing body fat, reducing body weight, lowering blood glucose, improving insulin resistance and leptin resistance, and increasing liver glycogen and muscle glycogen in tissues in subjects.

The following references generally relate to BAIBA and are incorporated herein by reference in their entireties:

H. Smith and B. Dymond, "The determination of β-aminoisobutyric acid in urine," 8(4) *Clinica Chimica Acta* 614 (July 1963).

Eivind Solem et al., "The absolute configuration of β-aminoisobutyric acid in human serum and urine," 50(3) *Clinica Chimica Acta* 393 (February 1974).

Caroline Maisonneuve et al., "Effects of zidovudine, stavudine and β-aminoisobutyric acid on lipid homeostasis in mice: possible role in human fat wasting," 9(5) *Antiviral Therapy* 801 (October 2004).

Karima Begriche et al., "β-aminoisobutyric acid prevents diet-induced obesity in mice with partial leptin deficiency," 16(9) *Obesity* 2053 (September 2008)

Lee D. Roberts et al., "βl-aminoisobutyric acid induces browning of white fat and hepatic β-oxidation and is inversely correlated with cardiometabolic risk factors," 19(1) *Cell Metabolism* 96 (January 2014).

Tae Woo Jung et al., "BAIBA attenuates insulin resistance and inflammation induced by palmitate or a high fat diet via an AMPK-PPARδ-dependent pathway in mice," 58(9) *Diabetologia* 2096 (September 2015).

Cheng-Xiang Shi et al., "βl-aminoisobutyric acid attenuates hepatic endoplasmic reticulum stress and glucose/lipid metabolic disturbance in mice with type 2 diabetes," 6 *Scientific Reports* 21924 (February 2016).

Harika Vemula et al., "Gaussian and linear deconvolution of LC-MS/MS chromatograms of the eight aminobutyric acid isomers," 516 *Analytical Biochemistry* 75 (January 2017).

Yukiko Kitase et al., "β-aminoisobutyric acid, L-BAIBA, is a muscle-derived osteocyte survival factor," 22(6) *Cell Reports* 1531 (February 2018).

Dmitrii A. Tanianskii et al., "Beta-aminoisobutyric acid as a novel regulator of carbohydrate and lipid metabolism," 11(3) *Nutrients* 524 (February 2019).

SUMMARY

Disclosed herein are nutritional and/or therapeutic compositions comprising BAIBA, and methods of using the same. The disclosed compositions are effective at enhancing the beneficial effects of regular exercise and/or obtaining the physiological benefits of exercise in the absence of regular exercise. In some embodiments, the disclosed compositions are orally administrable and the disclosed methods recite oral dosage forms. In various aspects, the disclosed methods include administration of BAIBA concurrent with an exercise regimen such that the administration of BAIBA and the exercise regimen display a synergistic effect relative to administration of BAIBA alone or exercise alone.

In one aspect of the present disclosure, a method for improving a benefit of an exercise regimen experienced by a subject is provided, comprising administering a composition comprising β-aminoisobutyric acid (BAIBA), or a pharmaceutically acceptable salt, polymer, ester, or acid thereof, to the subject, wherein the subject is engaged in an exercise regimen, and wherein the benefit of the exercise regimen is greater with administration of the composition than the same exercise regimen without administration of the composition.

In embodiments, the benefit is selected from the group consisting of: reduced body fat percentage, reduced weight, lowered blood glucose, decreased blood triglycerides, decreased total blood cholesterol, decreased blood very low-density lipoprotein, decreased blood low density lipoprotein, increased muscular glycogen storage capacity, increased hepatic glycogen storage capacity, improved leptin resistance, improved insulin resistance, and combinations thereof.

In embodiments, the exercise regimen may comprise endurance training, resistance training, or both. Non-limiting examples of exercise regimens that comprise endurance training include speed-walking, running, jogging, dancing, cycling, and stair-climbing. Non-limiting examples of exercise regimens that comprise resistance training include weight training, circuit training, isometric exercise, gymnastics, plyometrics, parkour, yoga, and Pilates.

In embodiments, the BAIBA is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or substantially all L-β-aminoisobutyric acid (L-BAIBA).

In embodiments, the composition may be administered orally. The composition may, but need not, be an ingestible composition. The ingestible composition may, but need not, be selected from the group consisting of a dietary supplement, a medicated feed, a nutraceutical composition, and a pharmaceutical composition. The ingestible composition may, but need not, be a pharmaceutical composition comprising L-BAIBA as an active pharmaceutical ingredient. The ingestible composition may, but need not, be selected from the group consisting of aqueous solutions, aqueous suspensions, capsules, drops, granules, liquids, mists, powders, syrups, tablets, functionalized foods, beverages, toothpastes, and sublingual articles.

In embodiments, the subject may be a human.

In embodiments, the subject may suffer from a disorder selected from the group consisting of pre-obesity, obesity, and hyperglycemia.

In embodiments, the composition is administered at least once per day for a period of at least about four weeks.

In embodiments, an amount of L-BAIBA administered to the subject may be about 5 mg/kg/day to about 200 mg/kg/day. A total amount of BAIBA administered to the subject per day may, but need not, be from about 500 mg to about 1,500 mg, or alternatively in any range having a lower bound of any whole number of milligrams from about 500 mg to about 1,500 mg and an upper bound of any whole number of milligrams from about 500 mg to about 1,500 mg.

In another aspect of the present disclosure, a method for providing a subject with a benefit associated with exercise is provided, the method comprising administering a composition comprising β-aminoisobutyric acid (BAIBA), or a pharmaceutically acceptable salt, polymer, ester, or acid thereof, to the subject, wherein the subject is not engaged in an exercise regimen.

In embodiments, the benefit may be selected from the group consisting of reduced body fat, reduced weight, lower blood glucose, decreased blood triglycerides, decreased total blood cholesterol, decreased blood very low-density lipoprotein, decreased blood low density lipoprotein, increased muscular glycogen storage capacity, increased hepatic glycogen storage capacity, improved leptin resistance, improved insulin resistance, and combinations thereof.

In embodiments, the BAIBA is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or substantially all L-β-aminoisobutyric acid (L-BAIBA).

In embodiments, the composition may be administered orally. The composition may, but need not, be an ingestible composition. The ingestible composition may, but need not, be selected from the group consisting of a dietary supplement, a medicated feed, a nutraceutical composition, and a pharmaceutical composition. The ingestible composition may, but need not, be a pharmaceutical composition comprising L-BAIBA as an active pharmaceutical ingredient. The ingestible composition may, but need not, be selected from the group consisting of aqueous solutions, aqueous suspensions, capsules, drops, granules, liquids, mists, powders, syrups, tablets, functionalized foods, beverages, toothpastes, and sublingual articles.

In embodiments, the subject may be a human.

In embodiments, the subject may suffer from a disorder selected from the group consisting of pre-obesity, obesity, and hyperglycemia.

In embodiments, the composition is administered at least once per day for a period of at least about four weeks.

In embodiments, an amount of L-BAIBA administered to the subject is about 5 mg/kg/day to about 200 mg/kg/day. A total amount of BAIBA administered to the subject per day may, but need not, be from about 500 mg to about 1,500 mg, or alternatively in any range having a lower bound of any whole number of milligrams from about 500 mg to about 1,500 mg and an upper bound of any whole number of milligrams from about 500 mg to about 1,500 mg.

In another aspect of the present disclosure, an ingestible composition is provided, comprising from about 250 mg to about 1,000 mg of β-aminoisobutyric acid (BAIBA).

In embodiments, the ingestible composition may comprise from about 500 mg to about 750 mg of BAIBA, or alternatively may comprise BAIBA in an amount in any range having a lower bound of any whole number of milligrams from about 250 mg to about 1,000 mg and an upper bound of any whole number of milligrams from about 250 mg to about 1,000 mg.

In embodiments, the BAIBA is at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or substantially all L-β-aminoisobutyric acid (L-BAIBA).

In embodiments, the ingestible composition may, but need not, be selected from the group consisting of a dietary supplement, a medicated feed, a nutraceutical composition, and a pharmaceutical composition. The ingestible composition may, but need not, be a pharmaceutical composition comprising L-BAIBA as an active pharmaceutical ingredient. The ingestible composition may, but need not, be selected from the group consisting of aqueous solutions, aqueous suspensions, capsules, drops, granules, liquids, mists, powders, syrups, tablets, functionalized foods, beverages, toothpastes, and sublingual articles.

While specific embodiments and applications have been illustrated and described, the present disclosure is not limited to the precise configuration and components described herein. Various modifications, changes, and variations which will be apparent to those skilled in the art may be made in the arrangement, operation, and details of the methods and systems disclosed herein without departing from the spirit and scope of the overall disclosure.

As used herein, unless otherwise specified, the terms "about," "approximately," etc., when used in relation to numerical limitations or ranges, mean that the recited limitation or range may vary by up to 10%. By way of non-limiting example, "about 750" can mean as little as 675 or as much as 825, or any value therebetween. When used in relation to ratios or relationships between two or more numerical limitations or ranges, the terms "about," "approximately," etc. mean that each of the limitations or ranges may vary by up to about 10%; by way of non-limiting example, a statement that two quantities are "approximately equal" can mean that a ratio between the two quantities is as little as 0.9:1.1 or as much as 1.1:0.9 (or any value therebetween), and a statement that a four-way ratio is "about 5:3:1:1" can mean that the first number in the ratio can be any value of at least 4.5 and no more than 5.5, the second number in the ratio can be any value of at least 2.7 and no more than 3.3, and so on.

The embodiments and configurations described herein are neither complete nor exhaustive. As will be appreciated, other embodiments are possible utilizing, alone or in combination, one or more of the features set forth above or described in detail below.

DETAILED DESCRIPTION

Figure 1:
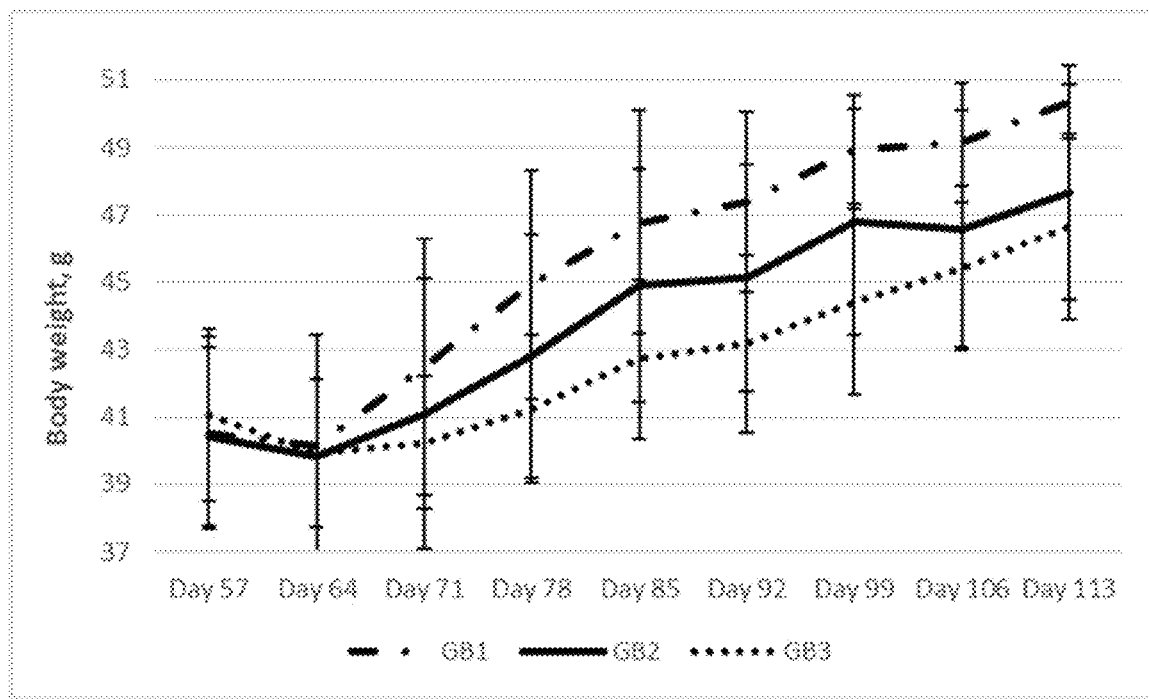
FIG. 1 is a graph of average body weight over time of three groups of mice, one of which ("GB3") received BAIBA supplementation and two of which ("GB1" and "GB2") did not, as described in Example 1 herein.
Figure 2A:
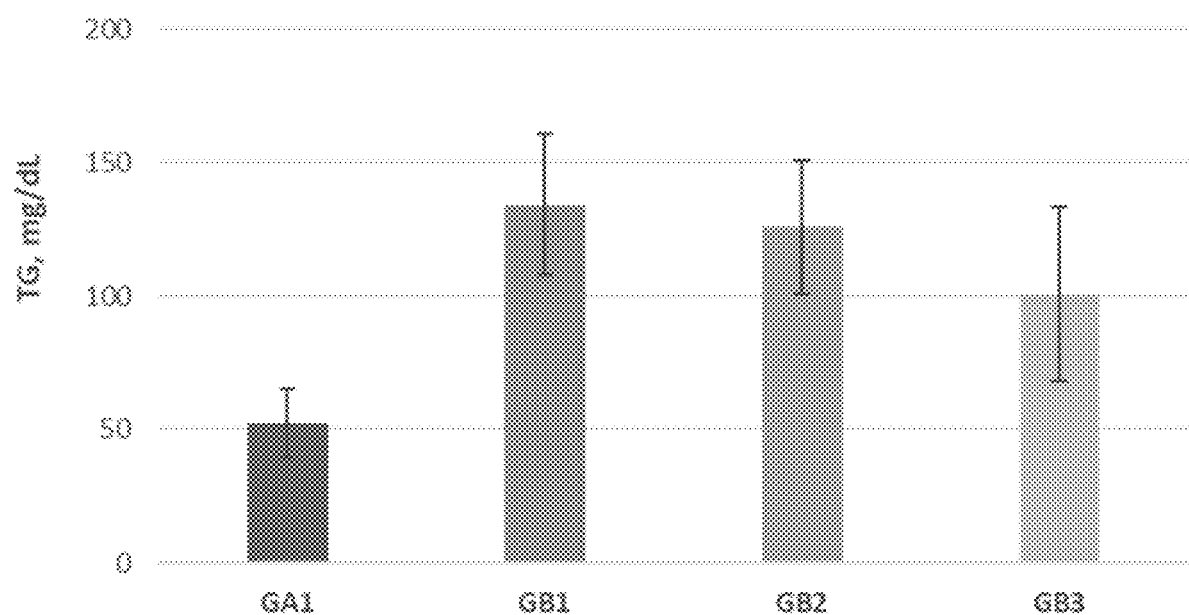
FIGS. 2A, 2B, 2C, and 2D are graphs of average blood levels of triglycerides, total cholesterol, low-density lipoprotein, and very low-density lipoprotein, respectively, in five groups of mice, two of which ("GB3" and "GB4") received BAIBA supplementation and three of which ("GA1," "GB1," and "GB2") did not, as described in Example 2 herein.
Figure 2B:
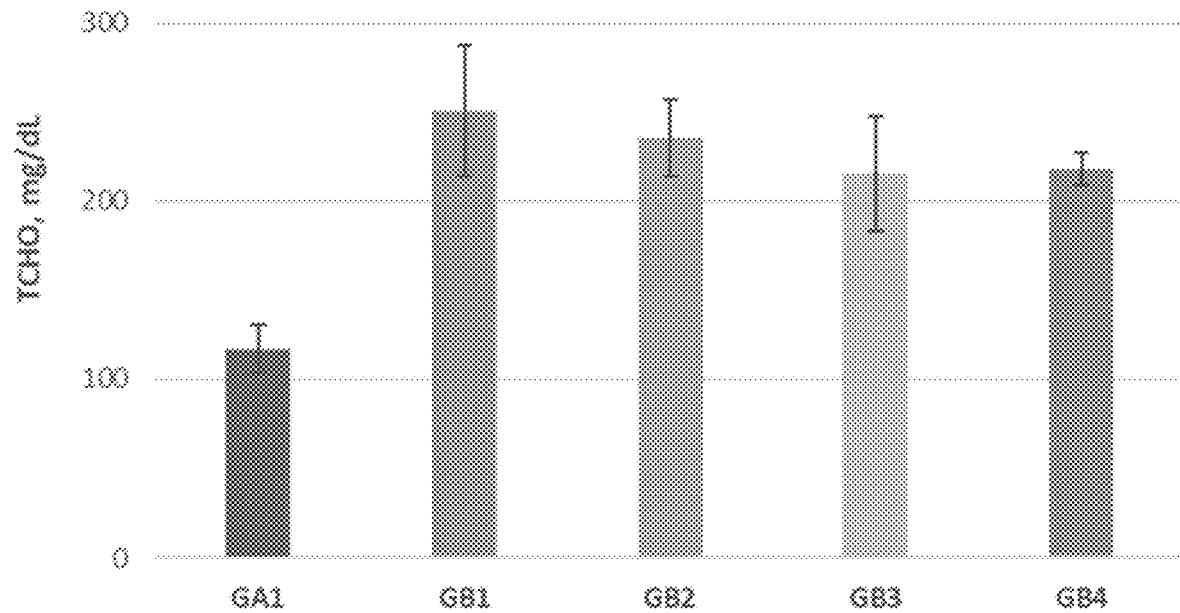
Figure 2C:
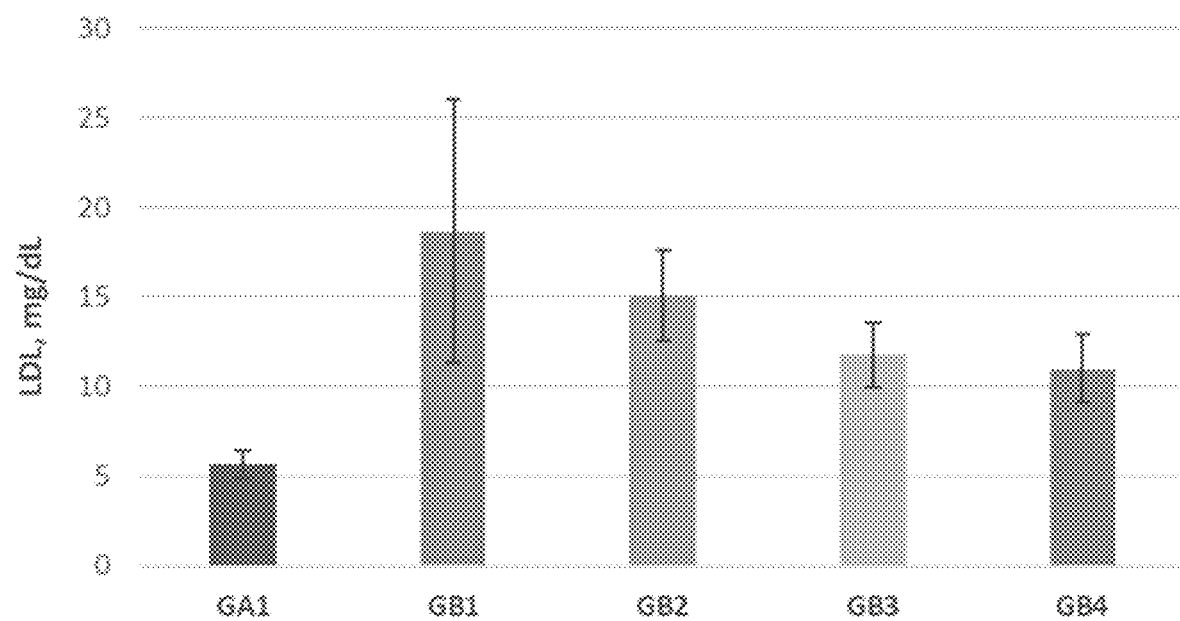
Figure 2D:
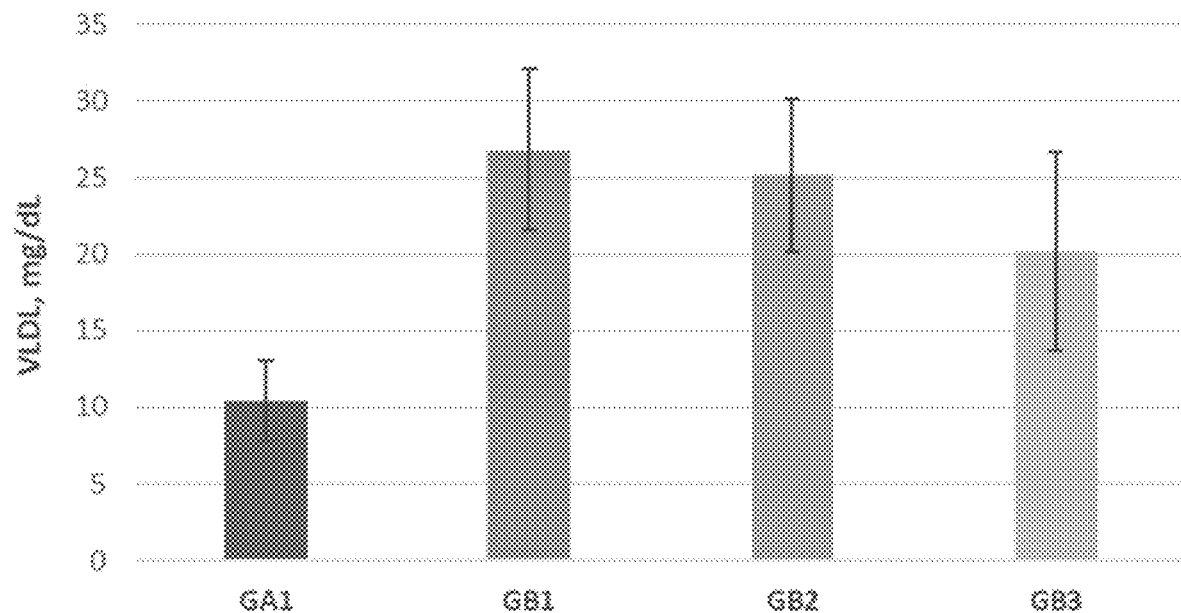

The terms "administering BAIBA" and "administration of BAIBA" as used herein include administration methods in which the BAIBA is directly administered to a subject, e.g., by putting the BAIBA directly into a dosage form that is administered to the subject, as well as methods in which the BAIBA is indirectly administered to a subject, e.g., by putting a precursor or prodrug of BAIBA directly into a dosage form that is administered to the subject.

As used herein, the term "ingestible composition" refers to a composition of matter that is adapted or configured to be consumed by an animal by taking the composition in through the mouth into the gastrointestinal tract, for example by eating or drinking. An "ingestible composition" as that term is used herein may be provided in a form selected from the group consisting of aqueous solutions, aqueous suspensions, capsules, drops, granules, liquids, mists, powders, syrups, tablets, functionalized foods, beverages, toothpastes, sublingual articles, and the like.

As used herein, the term "pharmaceutical composition" refers to a composition of matter comprising at least one active pharmaceutical ingredient that is adapted or configured to be administered to an animal for a therapeutic purpose.

As used herein, the term "subject" refers generally to an animal, including but not limited to a human, to which a composition or formulation provided by the present disclosure is administered or is to be administered. Other animals that may be "subjects" as those terms are used herein include but are not limited to companion animals, such as cats, dogs, and horses; livestock animals, such as cattle, goats, sheep, and pigs; mice; and rats.

Unless otherwise specified, all references to BAIBA or any enantiomer thereof herein encompass, in addition to BAIBA or the identified enantiomer in its base form, any and all pharmaceutically acceptable salts, polymers, esters, and acids thereof.

Embodiments of the present disclosure generally include an ingestible composition comprising β-aminoisobutyric acid (BAIBA). Embodiments of the present disclosure also include methods of administration of such compositions to a subject, which in some embodiments is a human, to treat a disease or condition and/or achieve a physiological objective. The compositions and methods exhibit advantageous efficiency and health benefits as compared to prior art BAIBA compositions and administration methods. The compositions and methods are generally provided to enhance the benefits of exercise and/or provide the benefits of exercise in the absence of regular exercise, but may also be useful to prevent and/or reduce the risk of developing a disease or condition, such as obesity.

Pharmaceutical compositions provided by the present disclosure may be formulated in a unit dosage form. A unit dosage form refers to a physically discrete unit suitable as a unitary dose for subjects undergoing treatment, with each unit containing a predetermined quantity of the active compound calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a subject at a single point in time or during a time interval.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some applications, maintaining a constant blood and tissue concentration throughout the course of therapy is the most desirable mode of treatment. Immediate release of drug may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of the active compound and/or the stability of the active compound in the gastrointestinal tract, the pharmacokinetics of the active compound and the intended therapeutic profile. An appropriate controlled release oral dosage form may be selected for a particular compound. For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of BAIBA upon oral administration. Sustained release oral dosage forms may be used to release drugs over a prolonged time period and are useful when it is desired that a drug or drug form be delivered to the lower gastrointestinal tract, including the colon. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

In certain embodiments, pharmaceutical compositions provided by the present disclosure may include any enteric-coated sustained release oral dosage form for administering the BAIBA. In one embodiment, the enteric-coated oral dosage form is administered to a subject at a dosing frequency of three times per day. In another embodiment, the enteric-coated oral dosage form is administered to a subject at a dosing frequency of twice per day. In still another embodiment, the enteric-coated oral dosage form is administered to a subject at a dosing frequency of once per day.

In certain embodiments, pharmaceutical compositions provided by the present disclosure may include any non enteric-coated sustained release oral dosage form for administering the BAIBA. In one embodiment, the non enteric-coated oral dosage form is administered to a subject at a dosing frequency of three times per day. In another embodiment, the non enteric-coated oral dosage form is administered to a subject at a dosing frequency of twice per day. In still another embodiment, the non enteric-coated oral dosage form is administered to a subject at a dosing frequency of once per day.

In certain embodiments, pharmaceutical compositions provided by the present disclosure may include any capsule oral dosage form for administering the BAIBA. In one embodiment, the capsule oral dosage form is administered to a subject at a dosing frequency of three times per day. In another embodiment, the capsule oral dosage form is administered to a subject at a dosing frequency of twice per day.

In still another embodiment, the capsule oral dosage form is administered to a subject at a dosing frequency of once per day.

A dose may be administered in a single dosage form or in multiple dosage forms. When multiple dosage forms are used the amount of compound contained within each dosage form may be the same or different. The amount of active compound contained in a dose may depend on the route of administration and whether the disease in a subject is effectively treated by acute, chronic, or a combination of acute and chronic administration.

One advantage of the present disclosure is that it may be utilized alone and/or it may be utilized in combination with, and thereby enhance the effectiveness of, other lifestyle changes in a subject. By way of non-limiting example, BAIBA compositions of the present disclosure may improve the effectiveness of an exercise regimen undertaken by the subject, but it may, additionally or alternatively, induce an exercise-like metabolic state in the subject even when the subject is not exercising, thus providing at least some of the benefits of exercise to the subject.

A significant advantage of the present disclosure is that the total dosage of BAIBA may be reduced relative to that needed to achieve similar results using BAIBA compositions of the prior art. As a result, compositions and methods of the present disclosure may be effective to treat or prevent a disease or condition, and/or achieve a physiological objective, in dosages of about half those needed to achieve the same results with prior art compositions and methods. In embodiments, suitable dosage amounts for the compositions and methods of the disclosure range from about 5 to about 200 mg/kg/day, or from about 5 to about 80 mg/kg/day, or from about 65 to about 140 mg/kg/day, or from about 125 to about 200 mg/kg/day. Suitable dosages for compositions of the present disclosure may be selected from a range having a lower limit selected from 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day, 60 mg/kg/day, 65 mg/kg/day, 70 mg/kg/day, 75 mg/kg/day, 80 mg/kg/day, 85 mg/kg/day, 90 mg/kg/day, 95 mg/kg/day, 100 mg/kg/day, 105 mg/kg/day, 110 mg/kg/day, 115 mg/kg/day, 120 mg/kg/day, 125 mg/kg/day, 130 mg/kg/day, 135 mg/kg/day, 140 mg/kg/day, 145 mg/kg/day, 150 mg/kg/day, 155 mg/kg/day, 160 mg/kg/day, 165 mg/kg/day, 170 mg/kg/day, 175 mg/kg/day, 180 mg/kg/day, 185 mg/kg/day, 190 mg/kg/day, and 195 mg/kg/day. Additionally or alternatively, suitable dosages for compositions of the present disclosure may be selected from a range having an upper limit selected from 200 mg/kg/day, 195 mg/kg/day, 190 mg/kg/day, 185 mg/kg/day, 180 mg/kg/day, 175 mg/kg/day, 170 mg/kg/day, 165 mg/kg/day, 160 mg/kg/day, 155 mg/kg/day, 150 mg/kg/day, 145 mg/kg/day, 140 mg/kg/day, 135 mg/kg/day, 130 mg/kg/day, 125 mg/kg/day, 120 mg/kg/day, 115 mg/kg/day, 110 mg/kg/day, 105 mg/kg/day, 100 mg/kg/day, 95 mg/kg/day, 90 mg/kg/day, 85 mg/kg/day, 80 mg/kg/day, 75 mg/kg/day, 70 mg/kg/day, 65 mg/kg/day, 60 mg/kg/day, 55 mg/kg/day, 50 mg/kg/day, 45 mg/kg/day, 40 mg/kg/day, 35 mg/kg/day, 30 mg/kg/day, 25 mg/kg/day, 20 mg/kg/day, 15 mg/kg/day, and 10 mg/kg/day.

In the methods of the treatment disclosed herein, the dosage may be varied during the course of treatment. In embodiments, two or more discrete dosage steps may be used, wherein a first dosage may be administered to the subject for a first period and a second dosage, which may be higher or lower than the first dosage, may be administered to the subject for a second period. By way of non-limiting example, the first and second dosages may be about 10 to about 200 mg/kg/day, and each of the first and second periods may be at least about one day, or at least about two days, or at least about three days, or at least about four days, or at least about five days, or at least about six days, or at least about one week, or at least about two weeks, or at least about three weeks, or at least about one month, or at least about two months, or at least about three months, or at least about four months, or at least about five months, or at least about six months, or at least about seven months, or at least about eight months, or at least about nine months, or at least about ten months, or at least about eleven months, or at least about one year. In embodiments, the dosage may also be continually ramped (i.e. gradually increased) or tapered (i.e. gradually decreased). The use of two or more distinct dosages, or of a ramped or tapered dosing regimen, may be beneficial where, by way of non-limiting example, it is desired to treat two or more diseases or conditions, simultaneously and/or sequentially, or where the severity of a disease or condition to be treated may vary over time.

Ingestible compositions of the present disclosure may be provided in any suitable form and physical manifestation. By way of non-limiting example, the ingestible composition can be administered to a subject as a dietary supplement, a medicated feed, a nutraceutical composition, and a pharmaceutical composition. By way of further non-limiting example, the ingestible compositions may be provided in any suitable physical form for oral administration, such as aqueous solutions or suspensions (e.g. an infused beverage, such as an energy beverage or energy "shot"), capsules (which may or may not be chewable), drops, granules, liquids, mists, powders, syrups, tablets (e.g. chewable, saliva-soluble, and/or swallowable tablets), functionalized foods (e.g. energy or nutrition bars, cookies, gums, candies, etc.), toothpastes, sublingual articles, and the like. In some embodiments, the composition may be provided in a form, e.g. a powder, that can be applied to a food (similar to a seasoning or condiment, etc.) or mixed with a beverage. Ingestible compositions of the present disclosure may thus comprise any suitable pharmaceutically acceptable additives, binders, and/or fillers, and may also comprise an active pharmaceutical or therapeutic agent other than BAIBA.

Ingestible compositions of the present disclosure may be provided as a unit dosage form that includes any suitable amount of BAIBA. By way of non-limiting example, an ingestible composition according to the present disclosure may be provided as an aliquot of an aqueous solution, an aliquot of an aqueous suspension, a capsule, a drop, a granule or plurality of granules, an aliquot of a liquid, an aliquot of a mist, an aliquot of a powder, an aliquot of a syrup, a tablet, a serving of a functionalized food, a serving of a beverage, an aliquot of a toothpaste, or a sublingual article, any of which may include an amount of BAIBA from about 250 mg to about 15 g, or alternatively in any range having a lower bound of any whole number of milligrams from about 250 mg to about 15 g and an upper bound of any whole number of milligrams from about 250 mg to about 15 g. In some embodiments, the unit dosage form may include BAIBA in an amount of about 250 mg, about 500 mg, about 750 mg, about 1 g, about 1.25 g, about 1.5 g, about 1.75 g, about 2 g, about 2.25 g, about 2.5 g, about 2.75 g, about 3 g, about 3.25 g, about 3.5 g, about 3.75 g, about 4 g, about 4.25 g, about 4.5 g, about 4.75 g, about 5 g, about 5.25 g, about 5.5 g, about 5.75 g, about 6 g, about 6.25 g, about 6.5 g, about 6.75 g, about 7 g, about 7.25 g, about 7.5 g, about 7.75 g, about 8 g, about 8.25 g, about 8.5 g, about 8.75 g, about 9 g, about 9.25 g, about 9.5 g, about 9.75 g, about 10 g, about 10.25 g, about 10.5 g, about 10.75 g, about 11 g, about 11.25 g, about 11.5 g, about 11.75 g, about 12 g, about 12.25 g, about 12.5 g, about 12.75 g, about 13 g, about 13.25 g, about 13.5 g, about 13.75 g, about 14 g, about 14.25 g, about 14.5 g, about 14.75 g, or about 15 g, or any amount in any range bounded by any two of these values.

The present inventors have found that administration of BAIBA to a subject in need thereof may treat a disease or condition and/or achieve a physiological objective in the subject more effectively than the compositions and methods of the prior art. Specifically, the cost, inconvenience, and risk of side effects to the subject may be reduced.

Preferred dosages and treatment lengths for the methods of the present disclosure may vary according to the particular disease or condition to be treated and/or the particular physiological objective to be achieved. By way of non-limiting example, administration of compositions containing BAIBA may be continued for an indefinite period of time, e.g. as a maintenance regimen, for the treatment or prevention of a chronic condition such as chronic hyperglycemia, or for continual or continuous enhancement of exercise performance. By way of further non-limiting example, administration of compositions containing BAIBA may be discontinued upon resolving an acute condition, e.g. acute hyperglycemia or acute ketosis, or upon achieving a physiological objective of treatment, e.g. reaching a target weight of the subject.

Another advantage of the present disclosure in relation to the manufacture of ingestible compositions comprising BAIBA is that the compositions of the present disclosure are characterized by a high degree of enantiomeric purity, i.e. a high content of a selected enantiomer of BAIBA. In many embodiments, it may be desirable to provide a high content of L-BAIBA and a low content of D-BAIBA, whereas in other embodiments it may be desirable to provide a high content of D-BAIBA and a low content of L-BAIBA. The BAIBA compositions of the present disclosure are also generally free of other chemical impurities. By way of non-limiting example, the BAIBA compositions of the prior art may generally provide BAIBA as a racemic mixture, i.e. a mixture of L-BAIBA and D-BAIBA in an approximate 50:50 ratio, whereas the BAIBA of compositions of the present disclosure may be at least about 1% L-BAIBA, at least about 2% L-BAIBA, at least about 3% L-BAIBA, at least about 4% L-BAIBA, at least about 5% L-BAIBA, at least about 10% L-BAIBA, at least about 15% L-BAIBA, at least about 20% L-BAIBA, at least about 25% L-BAIBA, at least about 30% L-BAIBA, at least about 35% L-BAIBA, at least about 40% L-BAIBA, at least about 45% L-BAIBA, at least about 50% L-BAIBA, at least about 55% L-BAIBA, at least about 60% L-BAIBA, at least about 65% L-BAIBA, at least about 70% L-BAIBA, at least about 75% L-BAIBA, at least about 80% L-BAIBA, at least about 85% L-BAIBA, at least about 90% L-BAIBA, at least about 95% L-BAIBA, at least about 96% L-BAIBA, at least about 97% L-BAIBA, at least about 98% L-BAIBA, at least about 99%, or substantially all L-BAIBA. The compositions and methods of the present disclosure thus exhibit significantly increased biological activity relative to the compositions and methods of the prior art.

In some embodiments, L-BAIBA may be more effective than D-BAIBA in providing a selected or desired benefit associated with an exercise regimen to a subject. In such embodiments, compositions may be provided in which at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or substantially all of the BAIBA is L-BAIBA. Providing a composition that has a high proportion of L-BAIBA may, in some embodiments, allow for the achievement of a physiological objective and/or the provision of a benefit to a subject while reducing the total amount of BAIBA administered to the subject relative to prior art compositions that may include a lower proportion of L-BAIBA (e.g. a racemic mixture of BAIBA), which may therefore enable one or more advantages or benefits, such as a reduction in the frequency of dosing, the risk of toxicity or side effects, and the like.

Alternatively, in some embodiments, D-BAIBA may be more effective than L-BAIBA in providing a selected or desired benefit associated with an exercise regimen to a subject. In such embodiments, compositions may be provided in which at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or substantially all of the BAIBA is D-BAIBA. Providing a composition that has a high proportion of D-BAIBA may, in some embodiments, allow for the achievement of a physiological objective and/or the provision of a benefit to a subject while reducing the total amount of BAIBA administered to the subject relative to prior art compositions that may include a lower proportion of D-BAIBA (e.g. a racemic mixture of BAIBA), which may therefore enable one or more advantages or benefits, such as a reduction in the frequency of dosing, the risk of toxicity or side effects, or the like.

The disclosure is further described by reference to the following non-limiting examples.

Example 1: Body Weight Reduction in Mice

36 C57BL/6 male mice aged about 8 weeks, each having a body mass of approximately 21 g, were randomly assigned to six study groups (GA1, GA2, GB1, GB2, GB3, and GB4) of six mice each. Each animal's body weight is measured by a weight scale and recorded.

The total experimental time is 16 weeks, divided into two periods: an eight-week induction period and an eight-week treatment period.

Each study group consisted of 6 animals, and treatment details of the individual study groups are given below:
  Group A1 (GA1): Normal mice, maintained on a normal diet (ND) for 8 weeks, receiving neither exercise nor L-BAIBA treatment.
  Group A2 (GA2): Normal mice, maintained on a normal diet (ND) for 8 weeks, receiving only L-BAIBA treatment and no exercise.
  Group B1 (GB1): Obese mice, maintained on a high-fat diet (HFD) for 8 weeks, receiving neither exercise nor L-BAIBA treatment.
  Group B2 (GB2): Obese mice, maintained on HFD for 8 weeks, receiving only exercise and no L-BAIBA treatment.
  Group B3 (GB3): Obese mice, maintained on HFD for 8 weeks, receiving only L-BAIBA treatment and no exercise.
  Group B4 (GB4): Obese mice, maintained on HFD for 8 weeks, receiving both L-BAIBA treatment and exercise.

Animals receiving L-BAIBA received, via oral administration, 150 mg/kg body weight of L-BAIBA, dissolved in 10 mL/kg body weight of ultrapure water, per day. Animals not receiving L-BAIBA were administered 10 mL/kg body weight of ultrapure water per day. All animals were maintained in a pathogen-free condition under a strict 12-hour alternate light/dark cycle with 12-15 cycles/hour of air exchange. All animals were provided with access to their respective feeds and water ad libitum. All animals were housed under controlled laboratory conditions of temperature and humidity at $23\pm2°$ C. and $50\pm10\%$ RH.

Throughout the study period, each mouse's body weight was measured weekly by a calibrated electronic digital weighing balance Sartorious BSA32025 (Sartorious AG, Göttingen, Germany). Over the course of the study, HFD-fed mice in groups receiving L-BAIBA supplementation, with or without exercise, underwent a greater reduction in body weight, relative to mice subjected to the same HFD, with or without exercise, that did not receive L-BAIBA supplementation. Particularly, mice in GB3 had reduced body weight relative to mice in GB1 and GB2, as illustrated in FIG. 1. This Example thus demonstrates that L-BAIBA supplementation can achieve, or even exceed, the beneficial effects on body weight of regular exercise. This effect persisted for as long as the test protocol was continued.

Example 2: Improvement in Metabolism-Related Biomarkers

At the end of the study described in Example 1, blood was collected from all test groups and various clinical parameters/biomarkers related to metabolism were determined: triglyceride (TG), total cholesterol (TCHO), low-density lipoprotein (LDL) and very low-density lipoprotein (VLDL). It was observed that HFD-fed mice in groups receiving L-BAIBA supplementation have lower levels of TG, TCHO, LDL, and VLDL relative to mice subjected to the same HFD, with or without exercise, that did not receive L-BAIBA supplementation. Particularly, mice in GB3 and GB4 had lower TG, TCHO, LDL, and VLDL levels relative to mice in GB1 and GB2, and mice in GB4 have lower TCHO and LDL levels relative to mice in GB1 and GB2; these results are illustrated in FIGS. 2A through 2D. This Example thus demonstrates that L-BAIBA supplementation without exercise can achieve, or even exceed, the beneficial effects on biomarkers related to metabolism (e.g. TG, TCHO, LDL, and VLDL) of regular exercise, and an exercise regimen combined with L-BAIBA supplementation can have a greater effect on these biomarkers than the exercise regimen alone.

Example 3: Increased Muscular and Hepatic Glycogen Storage Capacity

Figure 3A:
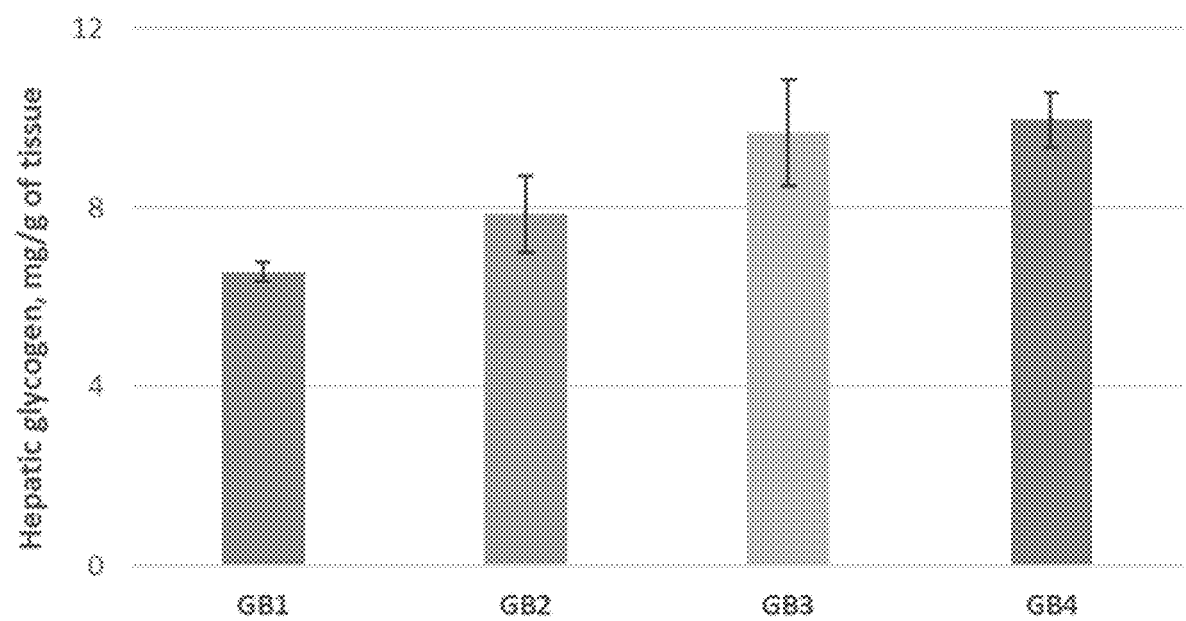
FIGS. 3A and 3B are graphs of average hepatic and muscular glycogen, respectively, in four groups of mice, two of which ("GB3" and "GB4") received BAIBA supplementation and two of which ("GB1" and "GB2") did not, as described in Example 3 herein.
Figure 3B:
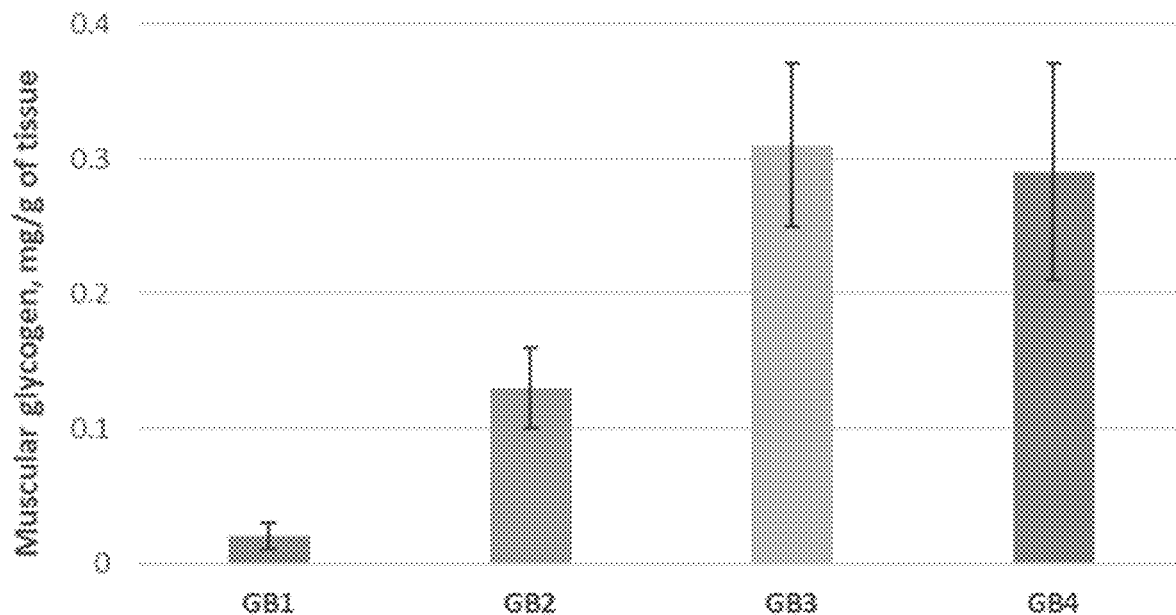

At the end of the study described in Example 1, the whole soleus muscle tissues and a sample of the main lobe of the liver of each mouse were used to measure glycogen content using a modified protocol as described in Methods in Enzymology Vol. III (Colowick and Kaplan, 1957). 200 mg/mL muscle and 50 mg/mL liver homogenates in 5% TCA were used. It was observed that HFD-fed mice in groups that received L-BAIBA supplementation had higher muscular and hepatic glycogen content relative to mice subjected to the same HFD, with or without exercise, that did not receive L-BAIBA supplementation. Particularly, mice in GB3 and GB4 had increased muscular and hepatic glycogen relative to mice in GB1 and GB2, as illustrated in FIGS. 3A and 3B. This Example thus demonstrates that L-BAIBA supplementation can achieve, or even exceed, the beneficial effects on muscular and hepatic glycogen storage capacity of regular exercise, and an exercise regimen combined with L-BAIBA supplementation can have a greater effect on muscular and hepatic glycogen storage capacity than the exercise regimen alone.

Example 4: Improved Leptin and Insulin Resistance

Figure 4A:
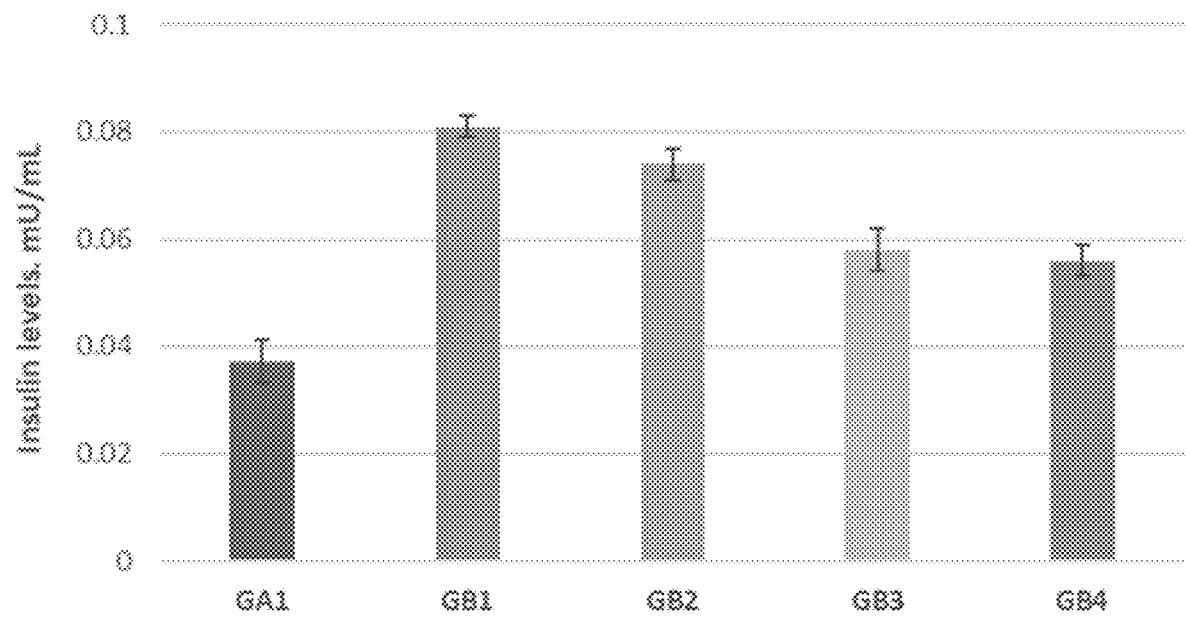
FIGS. 4A and 4B are graphs of average blood levels of insulin and leptin, respectively, in five groups of mice, two of which ("GB3" and "GB4") received BAIBA supplementation and three of which ("GA1," "GB1," and "GB2") did not, as described in Example 4 herein.
Figure 4B:
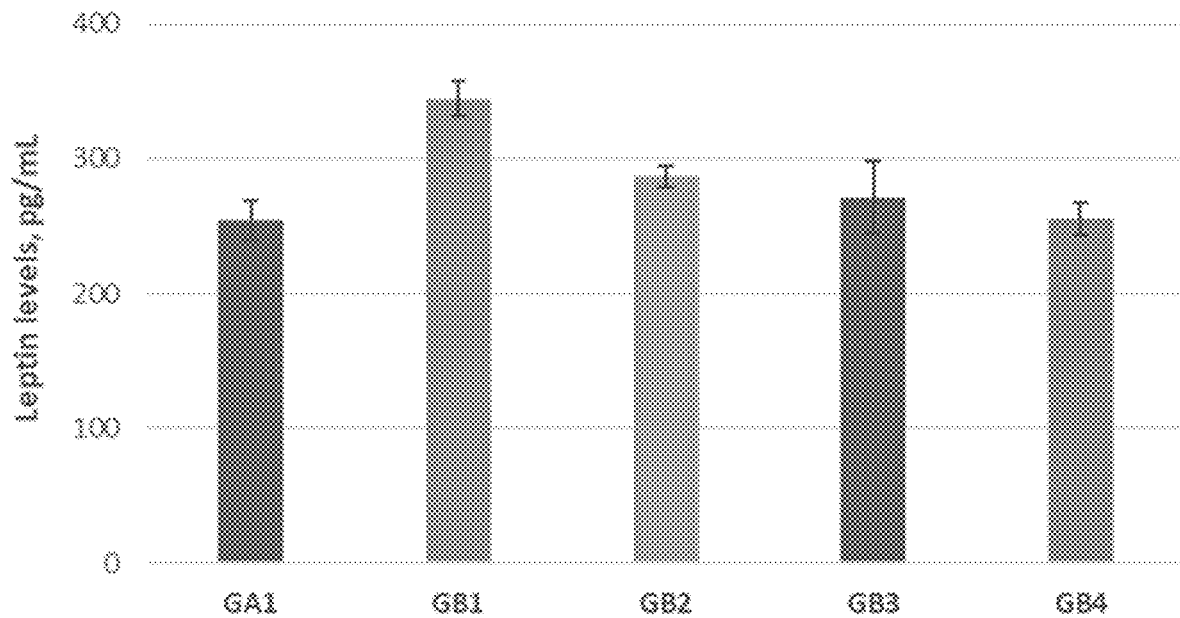
Figure 5A:
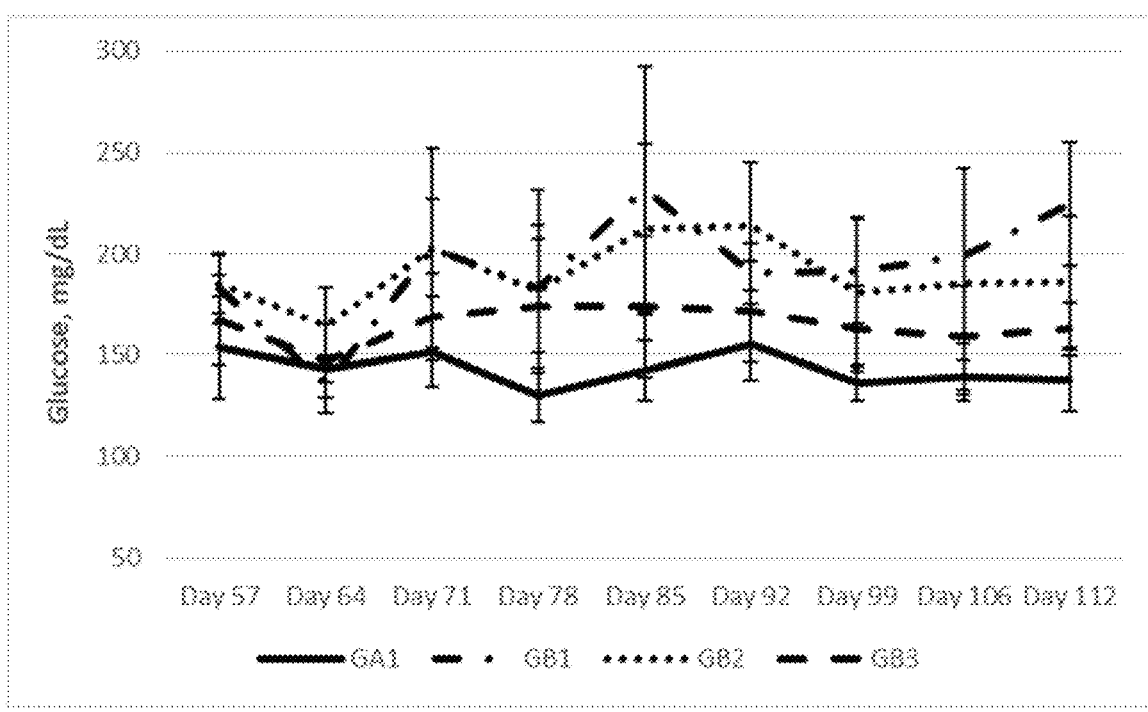
FIG. 5A is a graph of average blood glucose level over time of four groups of mice, one of which ("GB3") received BAIBA supplementation and three of which ("GA1," "GB1," and "GB2") did not, as described in Example 5 herein.
Figure 5B:
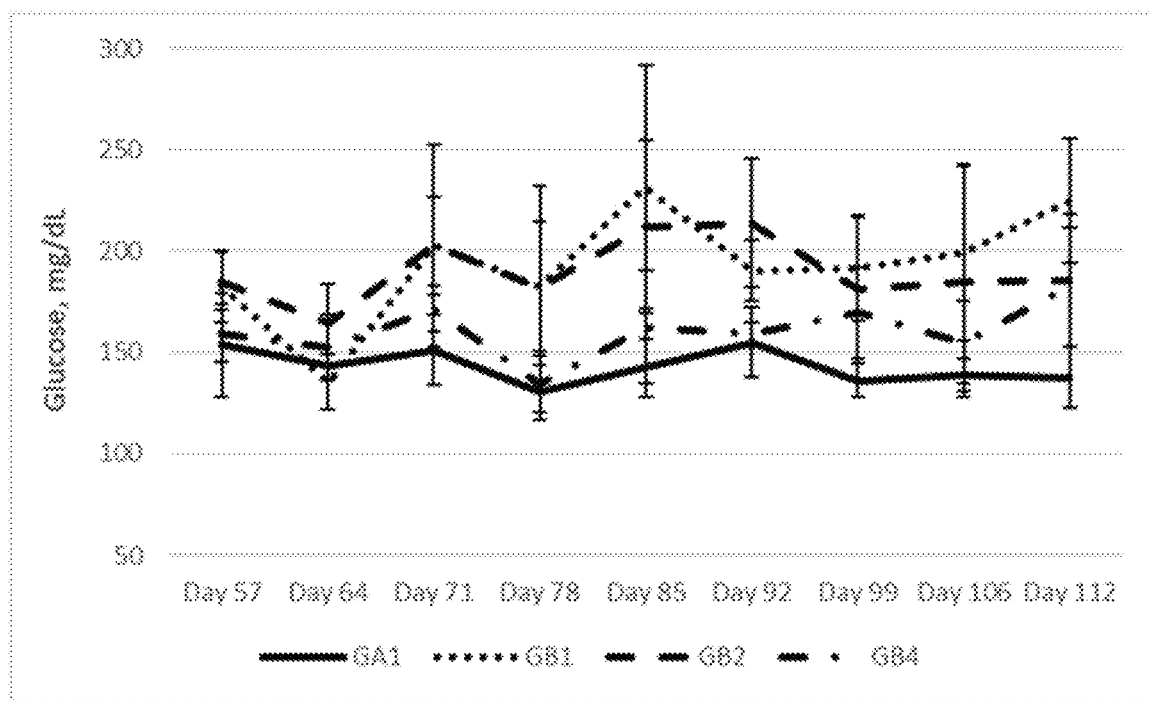
FIG. 5B is a graph of average blood glucose level over time of four groups of mice, one of which ("GB4") received BAIBA supplementation and three of which ("GA1" "GB1," and "GB2") did not, as described in Example 5 herein.
Figure 6A:
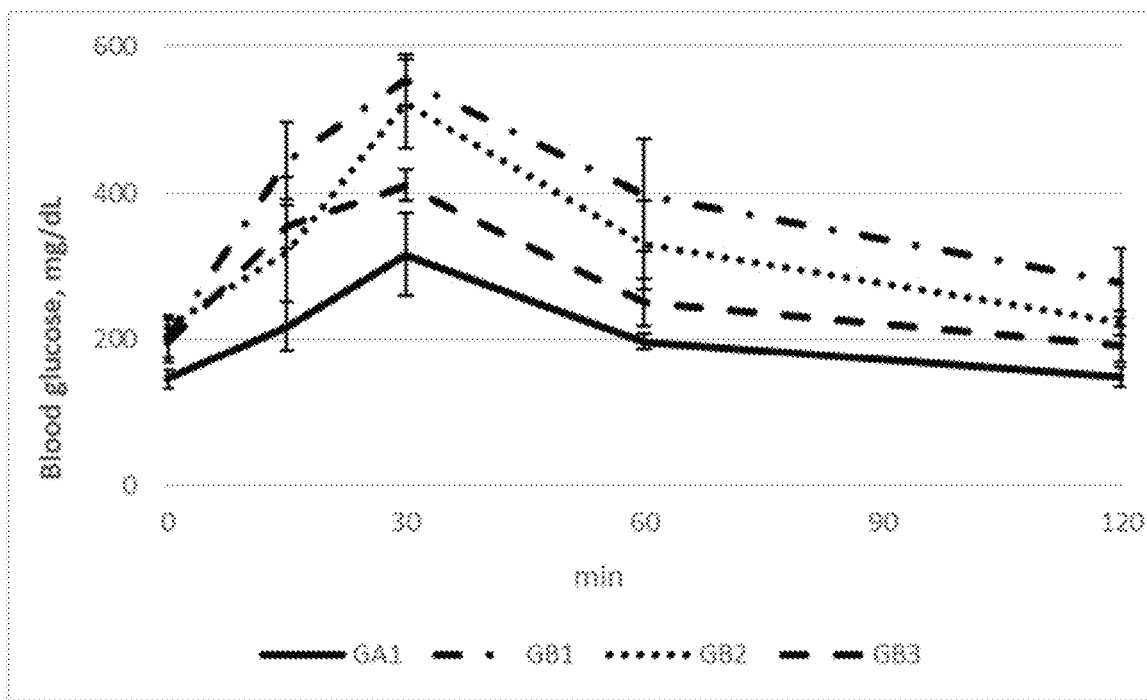
FIG. 6A is a graph of average blood glucose level during an oral glucose tolerance test (OGTT) of four groups of mice, one of which ("GB3") received BAIBA supplementation and three of which ("GA1" "GB1," and "GB2") did not, as described in Example 5 herein.
Figure 6B:
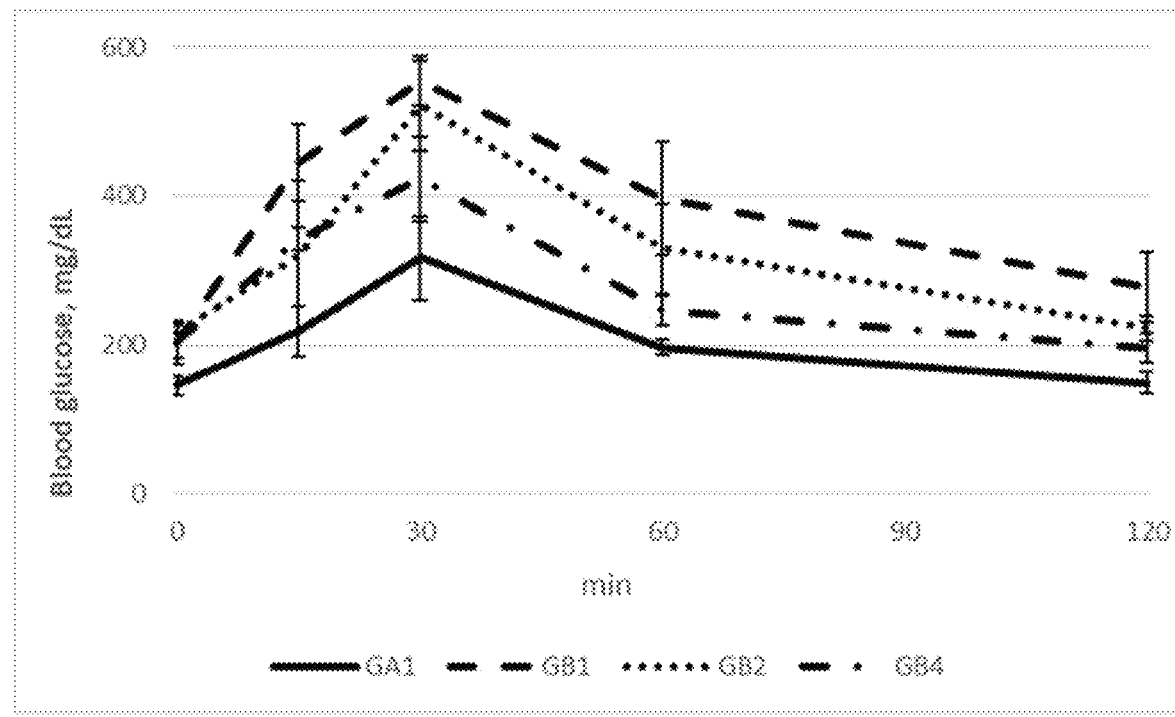
FIG. 6B is a graph of average blood glucose level during an OGTT of four groups of mice, one of which ("GB4") received BAIBA supplementation and three of which ("GA1" "GB1," and "GB2") did not, as described in Example 5 herein.
Figure 7:
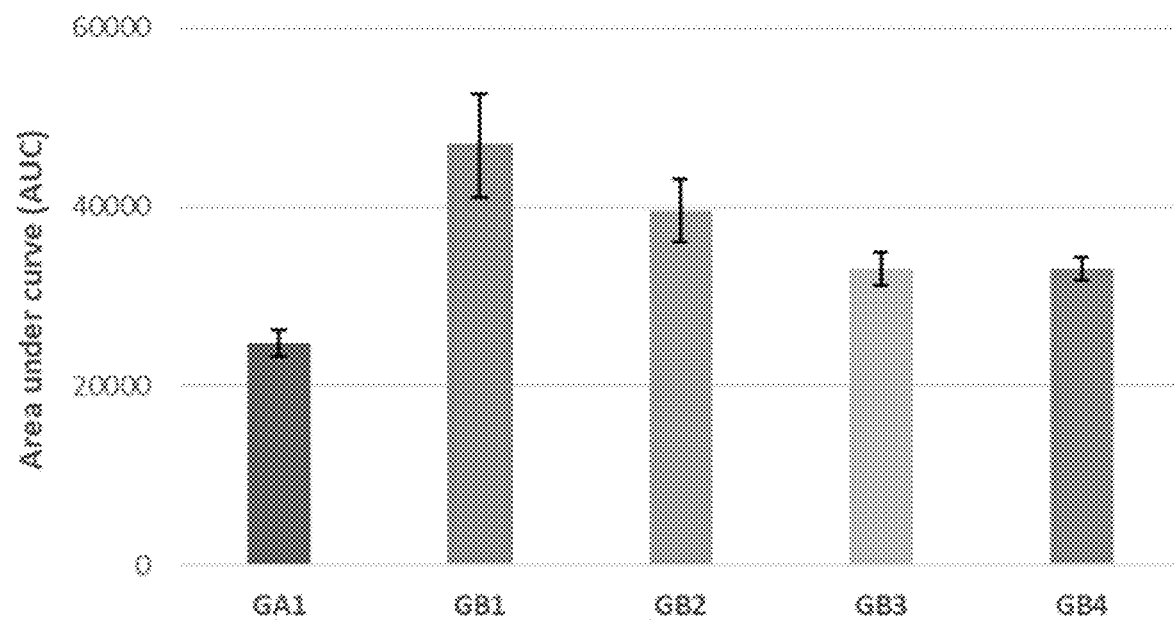
FIG. 7 is a graph of area under the curve of blood glucose level during an OGTT of five groups of mice, two of which ("GB3" and "GB4") received BAIBA supplementation and three of which ("GA1" "GB1," and "GB2") did not, as described in Example 5 herein.

At the end of the study described in Example 1, serum levels of insulin and leptin were quantified in all treatment groups by standard ELISA methods. Leptin is one of the major adipocytokines associated with maintaining glucose homeostasis. One key feature of obesity is the development of insulin and leptin resistance, resulting in an elevation of the circulating levels of these two hormones as a consequence of compensatory physiological responses to insulin and leptin insensitivity. It was observed that HFD-fed mice in groups that received L-BAIBA supplementation had improved leptin resistance and insulin resistance relative to mice subjected to the same HFD, with or without exercise, that did not receive L-BAIBA supplementation. Particularly, mice in GB3 and GB4 have improved leptin resistance (as illustrated in FIG. 4B) and insulin resistance (as illustrated in FIG. 4A) relative to mice in GB1 and GB2. This Example thus demonstrates that L-BAIBA supplementation can achieve, or even exceed, the beneficial effects on leptin and insulin resistance of regular exercise in obese mice, and an exercise regimen combined with L-BAIBA supplementation can have a greater effect on leptin resistance and insulin resistance of obese mice than the exercise regimen alone.

Example 5: Blood Glucose Reduction in Mice

Throughout the study described in Example 1, glucose levels in each mouse's blood were measured weekly (week 9-16) on the starting day of every week, before the day's exercise and L-BAIBA dosing activities. Blood was drawn from a tail vein of each mouse and the glucose levels were tested via strip-operated digital sensors, specifically using an SD CodeFree™ Glucometer (SD Biosensor Inc., South Korea). On day 113 (the day after the end of the treatment period of the study), an oral glucose tolerance test (OGTT) was performed for animals in both the ND and HFD groups. For the OGTT, animals were fasted for 2 hours and glucose (dextrose) was administered orally at 2 g/kg body weight in a dose volume (glucose dissolved in water) of 10 mL/kg. Blood glucose levels were monitored pre-dose and at 15, 30, 60 and 120 minutes after administration of the glucose solution. After 120 minutes, mice were returned to their respective cages and appropriate feed was provided per treatment group. The area under the curve (AUC) was calculated and expressed as percentage values.

Over the course of the study, mice in groups receiving L-BAIBA supplementation undergo a greater reduction in blood glucose level. Particularly, it was observed that L-BAIBA supplementation maintained the blood glucose level of obese mice at a stable level, close to the level of normal mice (GA1), throughout the experimental period, and that HFD-fed mice that received L-BAIBA supplementation showed better glucose tolerance relative to mice subjected to the same HFD, with or without exercise, that did not receive L-BAIBA supplementation. Particularly, mice in GB3 and GB4 underwent a greater reduction in blood glucose level relative to mice in GB1 and GB2, as illustrated in FIGS. 5A through 7. This Example thus demonstrates that L-BAIBA supplementation can achieve, or even exceed, the beneficial effects on blood glucose levels and glucose tolerance of regular exercise in obese mice, and an exercise regimen combined with L-BAIBA supplementation can have a greater effect on blood glucose levels and glucose tolerance in obese mice than the exercise regimen alone. This effect persisted for as long as the test protocol was continued.

The concepts illustratively disclosed herein suitably may be practiced in the absence of any element which is not specifically disclosed herein. It is apparent to those skilled in the art, however, that many changes, variations, modifications, other uses, and applications of the disclosure are possible, and also changes, variations, modifications, other uses, and applications which do not depart from the spirit and scope of the disclosure are deemed to be covered by the disclosure.

The foregoing discussion has been presented for purposes of illustration and description. The foregoing is not intended to limit the disclosure to the form or forms disclosed herein. In the foregoing Detailed Description, for example, various features are grouped together in one or more embodiments for the purpose of streamlining the disclosure. The features of the embodiments may be combined in alternate embodiments other than those discussed above. This method of disclosure is not to be interpreted as reflecting an intention that the claims require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment.

Moreover, though the description has included description of one or more embodiments and certain variations and modifications, other variations, combinations, and modifications are within the scope of the disclosure, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. A method for improving a benefit of an exercise regimen experienced by a subject, comprising:
    administering a composition comprising β-aminoisobutyric acid (BAIBA), or a pharmaceutically acceptable salt thereof, to the subject, wherein:
    the subject is engaged in an exercise regimen,
    a weight ratio of L-BAIBA to D-BAIBA in the composition is no less than 55/45, or a weight ratio of D-BAIBA to L-BAIBA in the composition is no less than 55/45, and
    the benefit of the exercise regimen is improved with administration of the composition relative to the same exercise regimen without administration of the composition.

2. The method of claim 1, wherein the benefit is selected from the group consisting of reduced body fat percentage, reduced weight, lower blood glucose, decreased blood triglycerides, decreased total blood cholesterols, decreased blood low density lipoprotein, decreased blood very low-density lipoprotein, improved leptin resistance, and improved insulin resistance, and combinations thereof.

3. The method of claim 1, wherein the exercise regimen comprises endurance training, resistance training, or both.

4. The method of claim 1, wherein the BAIBA is at least about 60%, at least about 65%, at least about 70%, at least about 75%, at least about 80%, at least about 85%, at least about 90%, at least about 95%, at least about 96%, at least about 97%, at least about 98%, at least about 99%, or substantially all L-β-aminoisobutyric acid (L-BAIBA).

5. The method of claim 1, wherein the composition is administered orally.

6. The method of claim 5, wherein the composition is an ingestible composition.

7. The method of claim 6, wherein the ingestible composition is selected from the group consisting of a dietary supplement, a medicated feed, a nutraceutical composition, and a pharmaceutical composition.

8. The method of claim 6, wherein the ingestible composition is a pharmaceutical composition comprising L-BAIBA as an active pharmaceutical ingredient.

9. The method of claim 6, wherein the ingestible composition is selected from the group consisting of aqueous solutions, aqueous suspensions, capsules, drops, granules, liquids, mists, powders, syrups, tablets, functionalized foods, beverages, toothpastes, and sublingual articles.

10. The method of claim 1, wherein the subject suffers from a disorder selected from the group consisting of pre-obesity, obesity, and hyperglycemia.

11. The method of claim 1, wherein the composition is administered at least once per day for a period of at least about four weeks.

12. The method of claim 1, wherein an amount of L-BAIBA administered to the subject is about 5 mg/kg/day to about 200 mg/kg/day.

13. The method according to claim 1, wherein the weight ratio of L-BAIBA to D-BAIBA in the composition is no less than 55/45.

14. The method according to claim 1, wherein the weight ratio of D-BAIBA to L-BAIBA in the composition is no less than 55/45.

15. The method according to claim 1, wherein the composition is administered to the subject concurrently engaged in the exercise regimen.

* * * * *